United States Patent [19]

Denny, Jr.

[11] 4,254,101

[45] Mar. 3, 1981

[54] TOOTHPASTE COMPOSITIONS

[75] Inventor: William D. Denny, Jr., Cincinnati, Ohio

[73] Assignee: The Procter & Gamble Company, Cincinnati, Ohio

[21] Appl. No.: 84,486

[22] Filed: Oct. 15, 1979

[51] Int. Cl.$^3$ .......................... A61K 7/16; A61K 7/18
[52] U.S. Cl. ........................................ 424/52; 424/49
[58] Field of Search ...................................... 424/49–58

[56] References Cited

U.S. PATENT DOCUMENTS

| | | | |
|---|---|---|---|
| 3,711,604 | 1/1973 | Colodney et al. | 424/52 |
| 3,911,104 | 10/1975 | Harrison | 424/52 |
| 3,919,409 | 11/1975 | Perca et al. | 424/52 |
| 3,927,202 | 12/1975 | Harvey et al. | 424/52 |
| 3,935,306 | 1/1976 | Roberts et al. | 424/52 |
| 3,980,767 | 9/1976 | Chown et al. | 424/52 |

*Primary Examiner*—Shep K. Rose
*Attorney, Agent, or Firm*—Douglas C. Mohl; Richard C. Witte; John V. Gorman

[57] ABSTRACT

Toothpastes containing a high level of humectant, a silica abrasive and a carboxyvinyl polymer and which possess excellent texture and appearance.

7 Claims, No Drawings

TOOTHPASTE COMPOSITIONS

TECHNICAL FIELD

This invention relates to novel, high humectant, toothpaste compositions which possess excellent texture as well as being stable in terms of their ability to provide therapeutic amounts of soluble fluoride for treatment of dental tissue. For purposes of this invention, the "soluble fluoride" content of any given toothpaste composition refers to the ppm concentration of fluoride ion which is found in a supernatant sample centrifuged from a 3:1 by weight slurry of the toothpaste in water (3:1=water:toothpaste).

Toothpastes containing high levels of humectant materials, relatively low levels of water, present particular thickenining problems. Many conventional binders such as carboxymethyl cellulose do not function well due to improper hydration. The improved fluoride stability of the present high humectant products is also important since fluoride ions are believed to interact with dental enamel to reduce the enamel's acid solubility.

It has been postulated that the effectiveness of fluoride toothpastes in providing enamel antisolubility benefits is dependent upon the amount of fluoride ion which is available for uptake by the enamel being treated. It is, of course, therefore desirable to formulate toothpaste products which provide maximum fluoride ion availability in brushing solutions formed therefrom.

Formulation of high humectant toothpastes which have acceptable texture is not accomplished without certain difficulties. As was noted earlier, many toothpaste binders are not acceptable for use in high humectant toothpastes due to their need for large amounts of water to hydrate properly. It has been surprisingly found that carboxyvinyl polymers function exceptionally well in such compositions.

BACKGROUND ART

Carboxyvinyl polymers have been suggested for use in toothpaste products in general but not in compositions of the type claimed herein. References disclosing carboxyvinyl polymer toothpastes include U.S. Pat. No. 3,980,767, Sept. 14, 1976 to Chown et al; U.S. Pat. No. 3,919,409, Nov. 11, 1975 to Perla et al; U.S. Pat. No. 3,911,904, Oct. 7, 1975 to Harrison; U.S. Pat. No. 3,711,604, Jan. 16, 1973 to Colodney et al; and U.S. Pat. No. 3,935,306, Jan. 27, 1976 to Roberts et al. As noted above, these references do not teach compositions containing relatively high levels of humectant, a silica abrasive and the carboxyvinyl polymer. Furthermore, the references do not suggest the advantages found by the present inventor for the present compositions.

Accordingly, it is an object of the present invention to provide toothpaste compositions which contain relatively high levels of humectant, silica dental abrasives and which possess excellent texture.

It is a further object of the present invention to formulate such toothpastes that exhibit superior fluoride stability.

DISCLOSURE OF THE INVENTION

The present invention relates to toothpaste compositions which exhibit excellent texture and if a fluoride ion source is present superior fluoride stability. Such compositions comprise a silica dental abrasive polishing material, a humectant, a carboxyvinyl polymer and water. Such toothpastes provide a pH of from about 4.0 to 8.0 when slurried with water in a 3:1 water/composition weight ratio.

The silica abrasive polishing materials comprise from about 6% to 45% by weight of the composition. Such abrasives can be any silica material having an average particle size of from about 0.1 to 30 microns.

The humectant comprises from about 30% to 70% by weight of the composition.

The carboxyvinyl polymer comprises from about 0.03% to 1.0% by weight of the composition.

The water in the toothpastes herein comprises from about 10% to 45% by weight of the composition.

DETAILED DESCRIPTION OF THE INVENTION

The toothpaste compositions of the present invention comprise a silica dental abrasive, a carboxyvinyl polymer binding agent, a humectant and water. Each of these components as well as optional ingredients, composition use and composition preparation are described in detail as follows.

SILICA ABRASIVE

The instant toothpaste compositions contain from about 6% to 45%, preferably from about 10% to 30%, by weight of a silica abrasive polishing material. Silica dental abrasives of various types can provide the unique benefits of exceptional dental cleaning and polishing performance without unduly abrading tooth enamel or dentin. Silica abrasive materials are also exceptionally compatible with sources of soluble fluoride.

The silica abrasive polishing material used herein generally has an average particle size ranging between about 0.1 to 30 microns, preferably 5 and 15 microns. The abrasive can be precipitated silica or silica gels such as the silica xerogels described in Pader et al; U.S. Pat. No. 3,538,230; issued Mar. 2, 1970 and incorporated herein by reference. Preferred are the silica xerogels marketed under the tradename "Syloid" by the W. R. Grace & Company, Davison Chemical Division. Especially preferred are the precipitated silica materials such as those marketed by the J. M. Huber Corporation under the tradename, "Zeodent", particularly the silica carrying the designation "Zeodent 119". The types of silica dental abrasives useful in the toothpastes of the present invention are described in more detail in DiGiulio, U.S. Pat. No. 3,862,307; issued Jan. 21, 1975, incorporated herein by reference.

CARBOXYVINYL POLYMER

The carboxyvinyl polymers particularly useful in the toothpastes described herein are made by B. F. Goodrich and designated by the trademarks "Carbopol 934", "Carbopol 940" and "Carbopol 941". These products each consist essentially of a colloidally water-soluble polymer of acrylic acid crosslinked with from about 0.75% to 2.0% of a cross-linking agent selected from the class consisting of pollyallyl sucrose and pollyallyl pentaerythritol.

The polymer is present in the compositions of the present invention at a level of from about 0.03% to 1.0%, preferably from about 0.2% to 0.5%.

HUMECTANT

Another essential component of the toothpaste compositions herein is a humectant. The humectant serves to keep the toothpaste compositions from hardening upon exposure to air. Certain humectants can also impart desirable sweetness or flavor to toothpaste compositions. The humectant, on a pure humectant basis, generally comprises from about 30% to 70%, preferably from about 45% to 65%, by weight of the toothpaste compositions herein.

Suitable humectants for use in this invention include edible polyhydric alcohols such as glycerine, sorbitol, xylitol and propylene glycol. Sorbitol is frequently employed as a 70% aqueous solution known as Sorbo ®. Mixtures of glycerine and sorbitol are especially preferred as the humectant component of the toothpaste compositions herein.

WATER

Water is another essential element of the toothpastes of this invention. Water employed in the preparation of commercially suitable toothpastes should preferably be deionized and free of organic impurities. Water comprises from about 10% to 45%, preferably from about 20% to 35%, by weight of the toothpaste compositions herein. These amounts of water include the free water which is added plus that which is introduced with other materials.

OPTIONAL INGREDIENTS

In addition to the above described essential components, the toothpastes of this invention can contain a variety of optional conventional toothpaste ingredients. Such optional ingredients include fluoride ion sources sudsing agents, flavoring agents, sweetening agents, anticalculus agents, antiplaque agents, coloring agents, A preferred optional ingredient in the instant compositions is a fluoride ion source at a level of from about 0.01% to 3%, preferably from about 0.03% to 1.0%, by weight of the compositions. Such fluoride ions combine with dental enamel and thereby reduce enamel solubility in acid. Application of fluoride ions to dental enamel serves to protect teeth against decay.

A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970 and Widder et al; U.S. Pat. No. 3,678,154; issued July 18, 1972, both patents being incorporated herein by reference. Preferred fluoride ion sources for use herein include sodium fluoride, stannous fluoride, potassium fluoride, potassium stannous fluoride ($SnF_2$-KF), indium fluoride, zinc fluoride, ammonium fluoride and stannous chlorofluoride. Sodium fluoride and stannous fluoride are particularly preferred, as well as mixtures thereof.

Preferably the instant toothpaste compositions provide from about 50 ppm to 10,000 ppm, more preferably from about 100 to 3000 ppm, of fluoride ions in the aqueous solutions which contact dental surfaces when the toothpastes of the present invention are used in the mouth. Such solutions are simulated by preparing 3:1 water/toothpaste slurries (by weight) of the toothpaste compositions herein and by subsequently centrifuging such slurries to obtain an aqueous supernatant. The fluoride ion concentration in such a supernatant is taken as a measure of the "soluble fluoride" provided by any given fluoride toothpaste composition.

Another preferred optional ingredient is a sudsing agent. Suitable sudsing agents are those which are reasonably stable and form suds throughout a wide pH range, i.e., non-soap anionic, nonionic, cationic, zwitterionic and amphoteric organic synthetic detergents. Sudsing agents of these types are described more fully in Agricola et al; U.S. Pat. No. 3,959,458; issued May 25, 1976 and in Haefele; U.S. Pat. No. 3,937,807; issued Feb. 10, 1976. Both of these patents are incorporated herein by reference.

Anionic sudsing agents useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be employed.

The nonionic sudsing agents which can be used in the toothpastes of the present invention can be broadly defined as compounds produced by the condensation of alkylene oxide groups (hydrophilic in nature) with an organic hydrophobic compound which may be aliphatic or alkylaromatic in nature. Examples of suitable nonionic sudsing agents include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

The zwitterionic synthetic sudsing aents useful in the toothpastes of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate.

The cationic sudsing agents useful in the toothpastes of the present invention can be broadly defined as quaternary ammonium compounds having one long alkyl chain containing from about 8 to about 18 carbon atoms such as lauryl trimethylammonium chloride; cetyl pyridinium chloride; cetyl trimethylammonium bromide; di-isobutylphenoxyethoxyethyl-dimethylbenzylammonium chloride; coconutalkyltrimethylammonium nitrite; cetyl pyridinium fluoride; etc. Especially preferred are the quaternary ammonium fluorides described in U.S. Pat. No. 3,535,421, Briner et al, issued Oct. 20, 1970, incorporated by reference hereinbefore, where said quaternary ammonium fluorides have detergent properties. The cationic sudsing agents can also act as germicides in certain of the toothpastes herein.

The amphoteric sudsing agents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water-solubilizing group, e.g., carboxylate, sulfonate, sulfate, phosphate, or phosphonate.

The sudsing agent can be present in the toothpaste compositions of this invention in an amount from 0.1% to 6% by weight of the total composition.

Flavoring agents can also be added to the instant compositions. Suitable flavoring agents include oil of wintergreen, oil of peppermint, oil of spearmint, oil of sassafras, and oil of clove. Sweetening agents which can be used include saccharin, dextrose, levulose, aspartame, D-tryptophan, dihydrochalcones and sodium cyclamate. Flavoring agents are generally used in toothpastes at levels of from about 0.01% to 2% by weight and sweetening agents at levels of from about 0.05% to about 2% by weight. Additional binders can also be used with the carboxyvinyl polymer in the present compositions. Such binders include xanthan gum and carrageenan (Irish moss, Viscarin ®). These binders are generally present at a level of from about 0.1% to 1%.

Phosphorus-containing anticalculus agents and/or bis-biguanide antiplaque agents can also optionally be added to the toothpastes of this invention. Phosphorus-containing anticalculus agents such as disodium ethane-1-hydroxy-1, 1-diphosphonate and related materials are described more fully in McCune et al; U.S. Pat. No. 3,488,419, issued Jan. 6, 1970, incorporated herein by reference. Bis-biguanide antiplaque agents such as chlorhexidine (1,6-bis[$N^5$-p-chlorophenyl-$N^1$-biguanido]hexane), the soluble and insoluble salts thereof and related materials such as 1,2-bis($N^5$-p-trifluoromethylphenyl-$N^1$-biguanido)ethane are described more fully in Haefele, U.S. Pat. No. 3,934,002, issued Jan. 20, 1976; Haefele, U.S. Pat. No. 3,937,807, issued Feb. 10, 1976; Procter & Gamble, Belgian Pat. No. 843,244, published Dec. 22, 1976 and Procter & Gamble, Belgian Pat. No. 844,764, published Jan. 31, 1977. These patents are incorporated herein by reference.

If present, the optional anticalculus and/or antiplaque agents generally comprise from about 0.01% to 2.5% by weight of the toothpaste compositions herein.

METHOD OF MANUFACTURE

Toothpaste compositions of the present invention are prepared using reasonably conventional toothpaste preparation techniques. For example, part of the humectant and the precipitated silica may be mixed together with a sweetener, a buffering agent and an opacifier (if these materials are present) to form one mixture. Some water and a fluoride source may be mixed together to form a solution which is added to the silica slurry. The carboxyvinyl polymer may then be mixed slowly through a screen to minimize lumping with part of the humectant and a second binder, if present, to form a gel slurry. The slurry is then milled prior to being added to the other toothpaste components. A suitable mill is a Tekmar mill offered by Tekmer Company, Cincinnati, Ohio.

Once prepared, the compositions herein provide a pH of from about 4.0 to 8.0, preferably 6.8 to 8.0; when said compositions are slurried with water in a 3:1 weight ratio of water to composition. Fluoride toothpastes providing pH values within the 6.8 to 8.0 range provide especially stable fluoride stability compared to toothpastes with pH values outside this range. Flavoring of toothpastes within this pH range is also comparatively easy.

COMPOSITION USE

Toothpaste compositions of the present invention are used in conventional manner. The toothpaste compositions or slurries thereof are brushed onto dental surfaces and subsequently rinsed away.

During use of the toothpaste herein in conventional manner, pastes or slurries generally contact dental surfaces for at least about 30 seconds. More preferably such pastes or slurries contact dental surfaces for at least about 60 seconds.

Several representative toothpastes of the present invention are set forth in the following examples. All percentages used herein are by weight unless otherwise designated.

EXAMPLE I

A toothpaste of the present invention having the following composition was formulated.

| | |
|---|---|
| Sorbitol (70% Aqueous) | 58.760 |
| Glycerine | 15.000 |
| $NaH_2PO_4 \cdot H_2O$ | 0.050 |
| $Na_2HPO_4 \cdot 2H_2O$ | 0.200 |
| Sodium Saccharin | 0.250 |
| Syloid 63* | 3.000 |
| Syloid 74* | 13.000 |
| Flavor | 0.920 |
| Water | 4.061 |
| Sodium Fluoride | 0.243 |
| Carbopol 940** | 0.250 |
| Xanthan Gum | 0.200 |
| Sodium Alkyl ($C_{12}$) Sulfate (28.8% Aqueous) | 4.000 |
| Color (1% Aqueous) | 0.066 |
| | 100.000 |

*Xerogel silica abrasives - W. R. Grace & Company, Davison Chemical Division.
**Carboxyvinyl polymer - B. F. Goodrich Company.

EXAMPLE II

Another toothpaste of the present invention having the following formula is formulated.

| | |
|---|---|
| Sorbitol (70% Aqueous) | 51.002 |
| Sodium Saccharin | 0.220 |
| Trisodium Phosphate | 1.100 |
| Titanium Dioxide | 0.600 |
| Water | 3.000 |
| Flavor | 1.060 |
| Precipitated Silica* | 20.000 |
| Glycerine | 18.000 |
| Carbopol 940 | 0.250 |
| Xanthan Gum | 0.500 |
| Sodium Alkyl ($C_{12}$) Sulfate (28.8% Aqueous) | 4.000 |
| Sodium Fluoride | 0.243 |
| Color | 0.025 |
| | 100.00 |

*Supplied by J. M. Huber Corporation having the designation "Zeodent 119".

EXAMPLE III

A third toothpaste of the present invention having the following formula is formulated.

| | |
|---|---|
| Sorbitol (70% Aqueous) | 50.197 |
| Sodium Saccharin | 0.120 |
| $Na_3PO_4 \cdot 12H_2O$ | 1.450 |
| $NaH_2PO_4 \cdot H_2O$ | 0.590 |
| Titanium Dioxide | 0.700 |
| Precipitated Silica* | 20.000 |
| Water | 3.000 |
| Sodium Fluoride | 0.243 |
| Glycerine | 18.000 |
| Carbopol 940 | 0.250 |
| Xanthan Gum | 0.500 |
| Flavor | 0.900 |
| Sodium Alkyl ($C_{12}$) Sulfate (28.8% Aqueous) | 4.000 |
| Color (1% Aqueous) | 0.050 |
| | 100.00 |

*As in Example II.

What is claimed is:

1. A toothpaste composition comprising:
   (A) from about 6% to 45% of a silica dental abrasive;
   (B) from about 30% to 70% of a humectant;
   (C) from about 0.03% to 1.0% of a carboxyvinyl polymer; and
   (D) from about 10% to 45% of water;
   said composition providing a pH of from about 4.0 to 8.0 when slurried with water in a 3:1 water/composition weight ratio.

2. A toothpaste composition in accordance with claim 1 which in addition contains from about 0.01% to 3% of a fluoride ion source selected from the group consisting of sodium fluoride, potassium fluoride, ammonium fluoride and mixtures thereof and wherein the pH provided by the composition is from about 6.8 to 8.0.

3. A toothpaste composition in accordance with claim 2 wherein the amount of silica abrasive is from about 10% to 30% and the amount of humectant is from about 45% to 60%.

4. A toothpaste composition in accordance with claim 3 which contains an additional toothpaste composition component selected from the group consisting of
   (A) from about 0.1% to 6% of a sudsing agent;
   (B) from about 0.01% to about 2% of a flavoring agent;
   (C) from about 0.05% to 2% of a sweetening agent;
   (D) from about 0.1% to 1.0% of an additional binder; and
   (E) mixtures of these additional toothpaste composition components.

5. A toothpaste composition in accordance with claim 4 wherein:
   (A) the sudsing agent is selected from the group consisting of water-soluble salts of alkyl sulfates, water-soluble salts of sulfonated monoglycerides and mixtures thereof; and
   (B) the humectant is selected from the group consisting of glycerine, sorbitol, xylitol and mixtures thereof.

6. A toothpaste composition in accordance with claim 5 wherein the fluoride ion source is sodium fluoride and wherein the additional binder is xanthan gum.

7. A toothpaste composition comprising:
   (A) from about 6% to 45% of a precipitated silica abrasive;
   (B) from about 30% to 70% of a humectant;
   (C) from about 0.03% to 1.0% of a carboxyvinyl polymer;
   (D) from about 0.01% to 3% of a fluoride ion source selected from the group consisting of sodium fluoride, potassium fluoride, ammonium fluoride and mixtures thereof; and
   (E) from about 10% to 45% of water;
   wherein said composition provides a pH of from about 6.8 to 8.0 when slurried with water in a 3:1 water/composition weight ratio.

* * * * *